US00PP37148P3

(12) United States Plant Patent
Kordes

(10) Patent No.: US PP37,148 P3
(45) Date of Patent: Dec. 16, 2025

(54) GRANDIFLORA ROSE PLANT NAMED 'KORdreimela'

(50) Latin Name: *Rosa hybrida*
Varietal Denomination: KORdreimela

(71) Applicant: W. KORDES' SÖHNE Rosenschulen GmbH & Co KG, Klein Offenseth-Sparrieshoop (DE)

(72) Inventor: Wilhelm-Alexander Kordes, Klein Offenseth-Sparrieshoop (DE)

(73) Assignee: W. KORDES' SÖHNE ROSENSCHULEN GMBH & CO KG, Klein Offenseth-Sparrieshoop (DE)

( * ) Notice: Subject to any disclaimer, the term of this patent is extended or adjusted under 35 U.S.C. 154(b) by 0 days.

(21) Appl. No.: 19/005,033

(22) Filed: Dec. 30, 2024

(65) Prior Publication Data

US 2025/0280742 P1 Sep. 4, 2025

(30) Foreign Application Priority Data

Apr. 4, 2024 (QZ) ..... PBR 10269

(51) Int. Cl.
*A01H 6/74* (2018.01)
*A01H 5/02* (2018.01)

(52) U.S. Cl.
USPC ..... Plt./134
CPC ..... *A01H 6/749* (2018.05); *A01H 5/02* (2013.01)

(58) Field of Classification Search
USPC ..... Plt./134
CPC ..... A01H 6/749; A01H 5/02
See application file for complete search history.

(56) References Cited

U.S. PATENT DOCUMENTS

PP23,551 P3 4/2013 Meilland
PP23,667 P2 6/2013 Kordes

*Primary Examiner* — Keith O. Robinson
(74) *Attorney, Agent, or Firm* — Panitch Schwarze Belisario & Nadel LLP; Stephany G. Small; Travis W. Bliss

(57) ABSTRACT

A new and distinct variety of grandiflora rose plant, referred to by its cultivar name, 'KORdreimela', is described. The new variety forms in abundance on a substantially continuous basis, yellow-colored blossoms. The growth habit is very bushy and upright. Glossy, medium green ornamental foliage is formed. Additionally, the new variety is particularly well suited for growing as distinctive ornamentation in the landscape.

1 Drawing Sheet

Latin name of genus and species of plant claimed: *Rosa hybrida.*

Variety denomination: 'KORdreimela'.

CROSS REFERENCE TO RELATED APPLICATIONS

This application claims priority to Plant Breeders' Right Application No. PT 10269, which was filed in South Africa with a date of application of Apr. 4, 2024, the contents of which are hereby incorporated by reference for all purposes.

STATEMENT REGARDING PRIOR DISCLOSURES BY THE INVENTOR

The first sale or offer for sale of the new variety was March 2024, in the Ludwig's Roses Catalog. The first sale or offer for sale of the new variety was by the inventor or another who obtained the new variety directly or indirectly from the inventor. No plants of the new variety have been sold in this country or anywhere in the world, nor has any disclosure of the new plant been made, more than one year prior the effective filing date of this application, and such sale or disclosure within one year was either derived directly or indirectly from the inventor.

BACKGROUND OF THE INVENTION

The new variety of grandiflora rose plant of the present invention was created by controlled breeding during May 2011, in Offenseth-Sparrieshoop, Germany by artificial pollination wherein two parents were crossed which previously had been studied in the hope that they would contribute the desired characteristics. The female parent (i.e., the seed parent) of the new variety was the 'KORlubaja' variety (U.S. Plant Pat. No. 23,667). The male parent (i.e., the pollen parent) of the new variety was an unnamed breeder seedling (not patented).

The parentage of the new variety can be summarized as follows:

'KORlubaja' x unnamed breeder seedling

The seeds resulting from the above pollination were sown and small plants were obtained which were physically and biologically different from each other. Selective study resulted in the identification of a single plant of the new variety.

The new variety has been found to undergo asexual propagation in Wasco, California and Cochranville, Pennsylvania by a number of routes such as vegetative cuttings. Asexual propagation techniques in Wasco, California and Cochranville, Pennsylvania, such as vegetative cuttings, have shown that the characteristics of the new variety are homogeneous, stable, and strictly transmissible by such asexual propagation from one generation to another. Accordingly, the new variety undergoes asexual propagation in a true-to-type manner.

SUMMARY OF THE INVENTION

It was found that the new variety of grandiflora rose plant of the present invention possesses the following combination of characteristics:

(a) forms yellow-colored blossoms, (b) exhibits a very bushy and upright growth habit, and (c) provides glossy, medium green foliage.

The new variety well meets the needs of the horticultural industry. It can be grown to advantage as ornamentation in parks, gardens, public areas, and residential landscapes. Accordingly, it is particularly well suited for growing in the landscape.

The new variety can be readily distinguished from its ancestors. More specifically, the new variety displays yellow-colored flowers and provides a more upright growth habit and higher petal count compared to the 'KORlubaja' variety (i.e., the seed parent), which has apricot orange-colored flowers. Additionally, the new variety forms a more pointed flower shape and exhibits improved vigor compared to the unnamed breeder seedling (i.e., the pollen parent). Moreover, the new variety can be readily distinguished from non-parental related similar varieties. For example, the new variety displays a higher petal count, exhibits a stronger and more noticeable fragrance, and holds the yellow flower color better without fading compared to the 'Meikanaro' variety (U.S. Plant Pat. No. 23,551).

The new variety has been named the 'KORdreimela' variety.

BRIEF DESCRIPTION OF THE PHOTOGRAPHS

The accompanying photograph shows, as nearly true as it is reasonably possible to make the same in a color illustration of this character, a typical specimen of the new variety and blossoms of the new variety. The illustrated rose plant of the new variety was approximately two years of age and was grown outdoors in a field in Arroyo Grande, California in April 2023.

Drawing—illustrates a specimen of the plant displaying flowers at varying points of opening.

DETAILED BOTANICAL DESCRIPTION

The chart used in the identification of colors is that of The Royal Horticultural Society (The R.H.S. Colour Chart, 2015 edition). The terminology which precedes reference to the chart has been added to indicate the corresponding color in more common terms and The R.H.S. Colour Chart designation used herein represents the closest color observed on the majority of the specified botanical feature. The description is based on a two-year-old specimen of the new variety, observed during September, while growing on its own roots in the ground in Cochranville, Pennsylvania.

Botanical classification: *Rosa hybrida* cultivar 'KORdreimela'.

Commercial classification: Grandiflora Rose.

Plant:

*Habit*.—Bushy and upright.

*Height*.—Typically 90.0 cm to 106.0 cm from the top of the soil plane when growing in the ground.

*Width*.—Approximately 78.0 cm on average.

Branches:

*Stem color*.—Old wood: Green Group 138A. — young stems: Green Group 143A.

*Length*.—Main stems: approximately 106.0 cm on average. — secondary stems: approximately 60.0 cm on average.

*Diameter*.—Main stems: approximately 1.4 cm on average. — secondary stems: approximately 5.0 mm on average.

*Texture*.—Smooth.

*Prickles*.—Amount: few to no prickles on top half of plant; 2 to 4 prickles per internode on main stems of lower half of plant. — young prickles: length is approximately 7.0 mm on average; width is approximately 8.0 mm on average at point of attachment; and color is Yellow-Green Group N144A. — old prickles: length is approximately 1.0 cm on average; width is approximately 7.0 mm on average at point of attachment; and color is Grey-Brown Group N199B at point of attachment, fading to Grey-Brown Group N199C at apex of prickle.

Leaflets:

*Number*.—3, 5, and 7.

*Shape*.—Ovate; apex is acute to acuminate; and base is cuneate.

*Arrangement*.—Odd-pinnate.

*Margin*.—Serrate.

*Undulation*.—Moderate.

*Glossiness of upper side*.—Semi-glossy.

*Texture*.—Upper surface: smooth. — under surface: smooth.

*Venation pattern*.—Reticulate.

*Size*.—Terminal leaflet: length is approximately 5.5 cm on average; width is approximately 4.4 cm on average. — lower leaflets: length is typically 3.5 cm to 5.0 cm; width is typically 2.5 cm to 4.0 cm. — 5-Leaflet leaf: length is approximately 10.0 cm on average; width is approximately 8.0 cm on average.

Foliage:

*Young foliage*.—Upper surface color: Green Group 141B with indistinguishable venation. — under surface color: Green Group 137B with venation of Green Group 138B.

*Old foliage*.—Upper surface color: Green Group 136A with indistinguishable venation. — under surface color: Green Group 137B with venation of Green Group 138B.

*Petiole*.—Texture: upper surface is hispidulous; under surface is thorny. — length: approximately 1.5 cm on average. — width: approximately 1.0 mm on average. — upper surface color: Green Group 139B. — under surface color: Green Group 143C.

*Rachis*.—Length: approximately 2.0 cm on average. — width: approximately 1.0 mm on average. — upper surface color: Green Group 139B. — under surface color: Green Group 143C.

*Stipules*.—Length: approximately 1.6 cm on average. — width: approximately 3.0 mm on average. — margin: entire to erose. — upper surface color: Green Group 143A. — lower surface color: Yellow-Green Group 146A.

Inflorescence:

*Number of flowers*.—About 20 to 25 blooms on average on a plant at once.

*Number of blossoms per stem or in a cluster*.—Typically 1 bloom per stem on average.

*Peduncle*.—Color: Green Group 143C. — diameter: approximately 1.0 mm on average. — length: approximately 4.0 cm on average. — surface texture: smooth.

*Sepals*.—Number: 5. — upper surface color and texture: Yellow-Green Group 144A with Green Group 143C at base, covered in short pubescence. — under surface color and texture: Green Group 139C with Green Group 139D at base, puberulent. — size: length is approximately 2.0 cm on average; width is approximately 4.0 mm on average. — margin: entire with extensions on most sepals measuring approximately 1.0 mm in length and 1.0 mm in width on average. — shape: lanceolate. — apex: acute to aristate. — base: truncate as it joins the receptacle.

*Buds*.—Shape: ovoid. — size: length is approximately 2.5 cm on average; width is approximately 1.7 cm on average. — color (when opening): Yellow Group 13A.

*Flower*.—Form: double, rosette. — profile: concave as it opens, and then outer petals are convex as the bloom ages and opens further. — diameter: approximately 7.5 cm on average. — height: approximately 5.0 cm on average. — duration: on the plant approximately 10 to 12 days. — petal color when first and fully opened: upper surface is Yellow Group 9A with no distinct basal spot; under surface is Yellow Group 9A with no distinct basal spot. — petal color at end of bloom: upper surface is Yellow Group 11B with a basal spot of Yellow Group 12A; under surface is Yellow Group 9A with a distinct basal spot of Yellow Group 12A. — petals reflex one by one: yes.

*Fragrance*.—Slight sweet scent.

*Petal*.—Number: 130 to 135 on average. — drop: average. — length: typically 3.0 cm to 4.5 cm. — width: typically 8.0 mm to 3.7 cm. — overall shape: broadly obovate. — margin: entire with moderate undulation. — apex shape: rounded to slightly cuspidate. — base shape: cuneate. — texture: upper surface is smooth; under surface is smooth.

*Petaloids*.—Number: approximately 4 on average. — length: approximately 1.0 cm on average. — width: approximately 3.0 mm on average. — color: upper and under surfaces are Yellow Group 9B with no visible basal spot. — texture: upper surface is smooth; under surface is smooth. — margin: entire. — shape: obovate. — apex: rounded to slightly cuspidate. — base: cuneate.

*Stamen*.—Number: approximately 13. — anthers: number is approximately 13; color is Yellow-Orange Group 17C; length is approximately 2.0 mm on average; and shape is oval. — filaments: length is approximately 5.0 mm on average and color is Yellow-Orange Group 17C.

*Pistils*.—Arrangement: separate and free. — number: approximately 45. — style: length is approximately 6.0 mm on average and color is Red Group 45C. — stigma: diameter is approximately 1.0 mm on average; shape is fan shaped; color is Orange-Red Group 34B.

*Receptacle*.—Diameter: approximately 1.0 cm on average. — depth: approximately 7.0 mm on average. — shape: urn shaped. — color: Yellow-Green Group 144B. — surface texture: smooth.

*Pollen*.—Amount: sparse. — color: Yellow-Orange Group 20A.

*Hips/seed*.—None observed.

Development:

*Vegetation*.—Semi-glossy, dark to medium green, and vigorous.

*Blossoming*.—Abundant and continuous from spring through frost; typically, in bloom outdoors from May to November in Southeastern Pennsylvania.

*Resistance to diseases*.—Very good resistance for powdery mildew (*Podosphaera pannosa*) and rust (*Phragmidium tuberculatum*).

*Hardiness*.—Hardy to USDA Zone 6; further hardiness testing is in progress.

The new 'KORdreimela' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of grandiflora rose plant named 'KORdreimela' characterized by the following combination of characteristics:

(a) forms yellow-colored blossoms, (b) exhibits a very bushy and upright growth habit, and (c) provides glossy, medium green foliage;

substantially as herein shown and described.

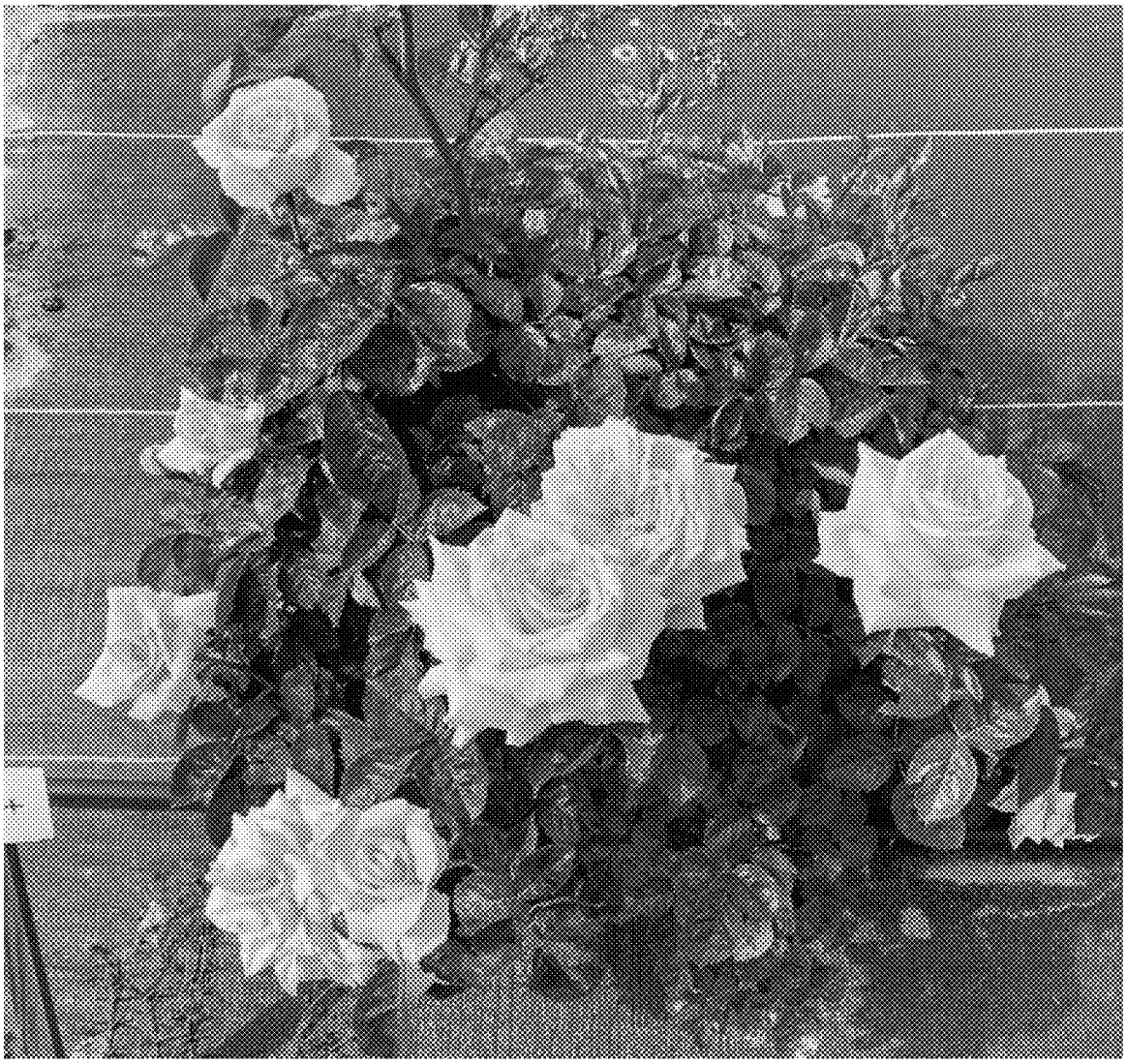

* * * * *